US010605775B2

(12) United States Patent
Haratani et al.

(10) Patent No.: US 10,605,775 B2
(45) Date of Patent: Mar. 31, 2020

(54) BIOSENSOR, METHOD FOR DETECTING BIOMOLECULES, AND BIOCHIP

(71) Applicant: TDK CORPORATION, Tokyo (JP)

(72) Inventors: Susumu Haratani, Tokyo (JP); Sachio Tsuboike, Tokyo (JP)

(73) Assignee: TDK CORPORATION, Tokyo (JP)

( * ) Notice: Subject to any disclaimer, the term of this patent is extended or adjusted under 35 U.S.C. 154(b) by 20 days.

(21) Appl. No.: 15/769,096

(22) PCT Filed: Nov. 8, 2016

(86) PCT No.: PCT/JP2016/083024
§ 371 (c)(1),
(2) Date: Apr. 18, 2018

(87) PCT Pub. No.: WO2017/082227
PCT Pub. Date: May 18, 2017

(65) Prior Publication Data
US 2018/0299407 A1 Oct. 18, 2018

(30) Foreign Application Priority Data

Nov. 10, 2015 (JP) .................. 2015-220728
Jun. 24, 2016 (JP) .................. 2016-125961

(51) Int. Cl.
*G01N 27/74* (2006.01)
*C12M 1/00* (2006.01)
(Continued)

(52) U.S. Cl.
CPC .............. *G01N 27/745* (2013.01); *C12M 1/00* (2013.01); *C12Q 1/68* (2013.01); *G01N 33/50* (2013.01);
(Continued)

(58) Field of Classification Search
CPC .... G01N 27/745; G01N 33/50; G01N 33/574; G01N 33/56983; G01R 33/1269;
(Continued)

(56) References Cited

U.S. PATENT DOCUMENTS 3,879,658 A 4/1975 Hummel
8,400,146 B2 3/2013 Kim et al.
(Continued)

FOREIGN PATENT DOCUMENTS

| JP | S49-094399 A | 9/1974 |
|---|---|---|
| JP | 2005-513475 A | 5/2005 |
| JP | 2012-507735 A | 3/2012 |

OTHER PUBLICATIONS

Jan. 31, 2017 International Search Report issued in Patent Application No. PCT/JP2016/083024.

*Primary Examiner* — Farhana A Hoque
(74) *Attorney, Agent, or Firm* — Oliff PLC

(57) ABSTRACT

A sensor includes: a substrate; a first magnetoresistance element and a second magnetoresistance element, each of which is a magnetoresistance element whose resistance value measured changes depending on a direction of an input magnetic field; and a soft magnetic thin film disposed adjacent to the first and second magnetoresistance elements wherein one of the first and second magnetoresistance elements is positioned on one of end sides of the soft magnetic thin film and other of the first and second magnetoresistance elements is positioned on other of the end sides of the soft magnetic thin film in a plan view in a direction perpendicular to a film surface of the soft magnetic thin film.

6 Claims, 8 Drawing Sheets

(51) Int. Cl.
*C12Q 1/68* (2018.01)
*G01N 33/50* (2006.01)
*G01R 33/09* (2006.01)
*G01R 33/12* (2006.01)
*G01N 33/569* (2006.01)
*G01N 33/574* (2006.01)
*C12Q 1/6825* (2018.01)

(52) U.S. Cl.
CPC ....... *G01R 33/098* (2013.01); *G01R 33/1269* (2013.01); *C12Q 1/6825* (2013.01); *G01N 33/56983* (2013.01); *G01N 33/574* (2013.01)

(58) Field of Classification Search
CPC ...... G01R 33/098; C12Q 1/68; C12Q 1/6825; C12M 1/00
USPC .......................................... 324/228; 73/53.01
See application file for complete search history.

(56) References Cited

U.S. PATENT DOCUMENTS

| | | | |
|---|---|---|---|
| 2005/0087000 A1* | 4/2005 | Coehoorn | B82Y 25/00 |
| | | | 73/53.01 |
| 2009/0146231 A1* | 6/2009 | Kuper | G01R 33/07 |
| | | | 257/421 |
| 2010/0109657 A1 | 5/2010 | Voegeli | |
| 2014/0228227 A1 | 8/2014 | Litvinov et al. | |

\* cited by examiner

FIG. 6
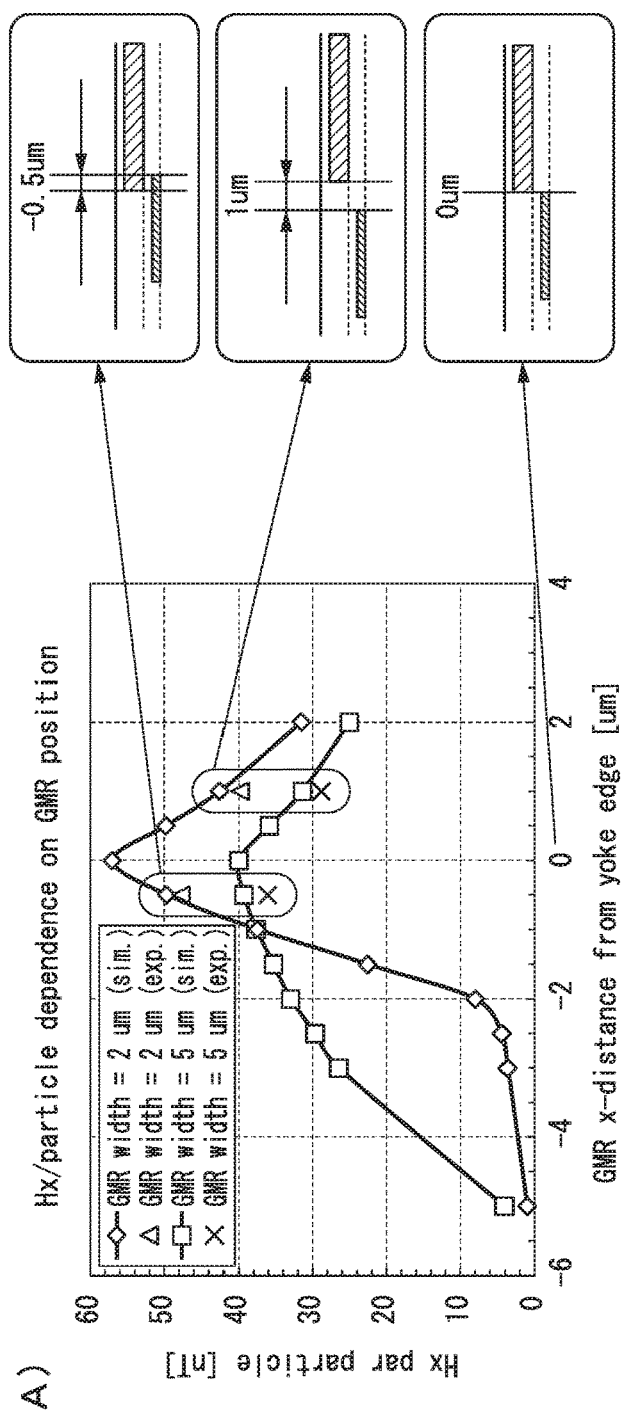
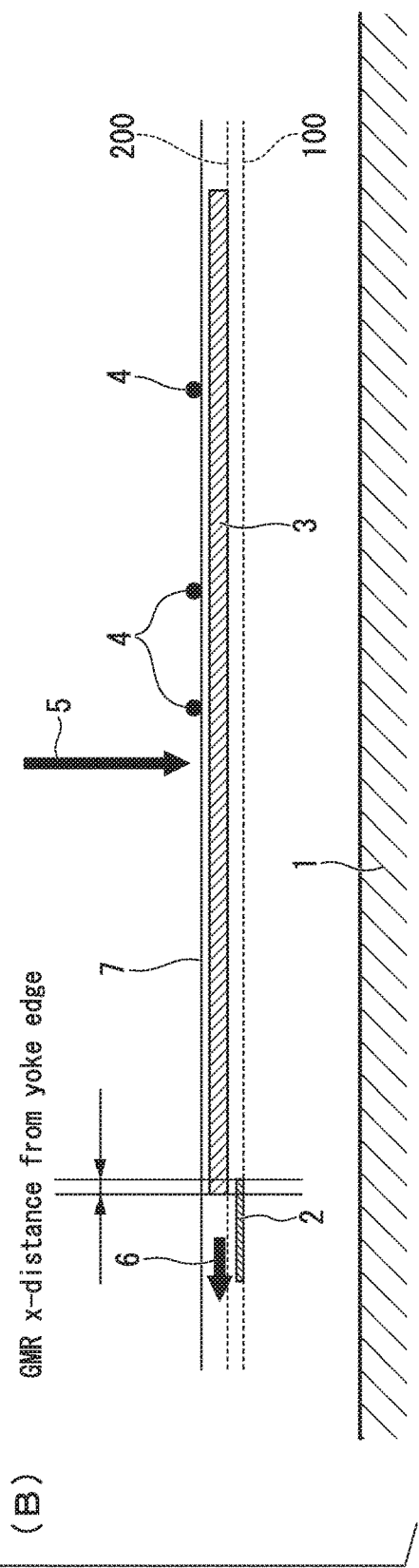

BIOSENSOR, METHOD FOR DETECTING BIOMOLECULES, AND BIOCHIP

TECHNICAL FIELD

The present invention relates to a biosensor, a method for detecting biomolecules, and a biochip.

Priority is claimed on Japanese Patent Application No. 2015-220728, filed on Nov. 10, 2015, and Japanese Patent Application No. 2016-125961, filed on Jun. 24, 2016, the contents of which are incorporated herein by reference.

BACKGROUND ART

A magnetoresistance element such as a giant magnetoresistance (GMR) element, a magnetic tunnel junction (TMR) element, or an anisotropic magnetoresistance (AMR) is often used as a magnetic sensor (see Published Japanese Translation No. 2005-513475 of the PCT International Publication). The magnetoresistance element is an element whose output resistance value changes depending on an input magnetic field. The change in the detected magnetic field can be measured according to the output resistance value.

FIGS. 7 and 8 are diagrams showing a conventional biosensor 500. As shown in FIG. 7, the biosensor 500 includes a substrate 101, a magnetoresistance element 102, a protective film 107, and a biomolecule capture layer 109 for capturing target biomolecules in this order. In the case where biomolecules in a sample are captured by the biomolecule capture layer 109, magnetic beads having an affinity for the biomolecules are captured on the biomolecule capture layer 109 through the biomolecules, and then a magnetic field is horizontally applied (applied magnetic field 105), a stray magnetic field 111 is generated from magnetic beads 104, and the stray magnetic field 111 is input to a magnetoresistance element 102.

FIG. 8 is a diagram showing the details of a conventional magnetoresistance element 102 used in a conventional biosensor 500. As shown in FIG. 8, the magnetoresistance element 102 has a set of three meander structures.

As shown in FIG. 7, in the conventional biosensor 500, since the application direction of the external magnetic field coincides with the magnetosensitive direction of the magnetoresistance element 102, in the case where the applied magnetic field 105 as an external magnetic field is strengthened in order to increase the stray magnetic field 111 from the magnetic beads 104, there has been a problem that the magnetization of the magnetosensitive layer of the magnetoresistance element is saturated and therefore the required output could not be obtained.

As shown in FIG. 8, in the case of the meander structure, there are a case where the magnetic beads 104 are disposed on the magnetoresistance elements 102 and a case where the magnetic beads 104 are disposed between the magnetoresistance elements 102. Since the output changes due to differences in placement, that is, due to the relative position of the magnetoresistance elements 102 and the magnetic beads 104, there has been a problem that sufficient accuracy could not be obtained because of variations in the measurement value of the quantity or concentration of the magnetic beads.

SUMMARY

It is desirable to provide a sensor, comprising: a substrate; a first magnetoresistance element and a second magnetoresistance element, each of which is a magnetoresistance element whose resistance value measured changes depending on a direction of an input magnetic field; and a soft magnetic thin film disposed adjacent to the first and second magnetoresistance elements wherein one of the first and second magnetoresistance elements is positioned on one of end sides of the soft magnetic thin film and other of the first and second magnetoresistance elements is positioned on other of the end sides of the soft magnetic thin film in a plan view in a direction perpendicular to a film surface of the soft magnetic thin film.

BRIEF DESCRIPTION OF DRAWINGS

FIG. 6(A) shows the results of Example 3 and FIG. 6(B) is a cross-sectional view showing an example of a biosensor used in Example 3.

DESCRIPTION OF EMBODIMENTS

Embodiments of the biosensor of the disclosure will be described.

It is to be noted that such embodiments will be described in detail in order to better understand the gist of the disclosure, and should not be construed as limiting the disclosure unless otherwise specified.

As used herein, the term "biosensor" refers to a sensor that senses a biomaterial (which may be naturally occurring or may be chemically synthesized), such as an enzyme, an antigen, an antibody, or a nucleic acid (including not only DNA and RNA, but also an artificial nucleic acid such as LNA).

[Biosensor]
<First Embodiment>

Figure 1:
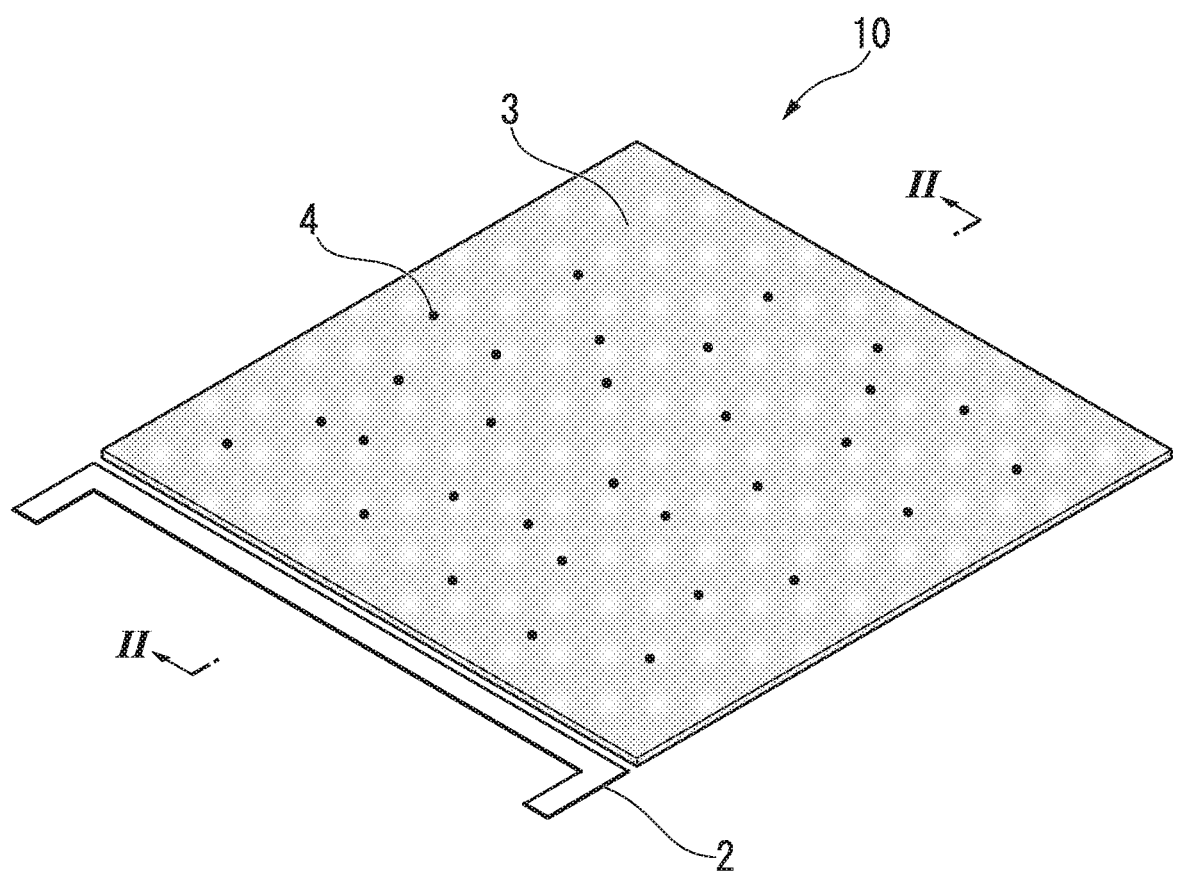
FIG. 1 is a perspective view of a biosensor according to a first embodiment.
Figure 2:
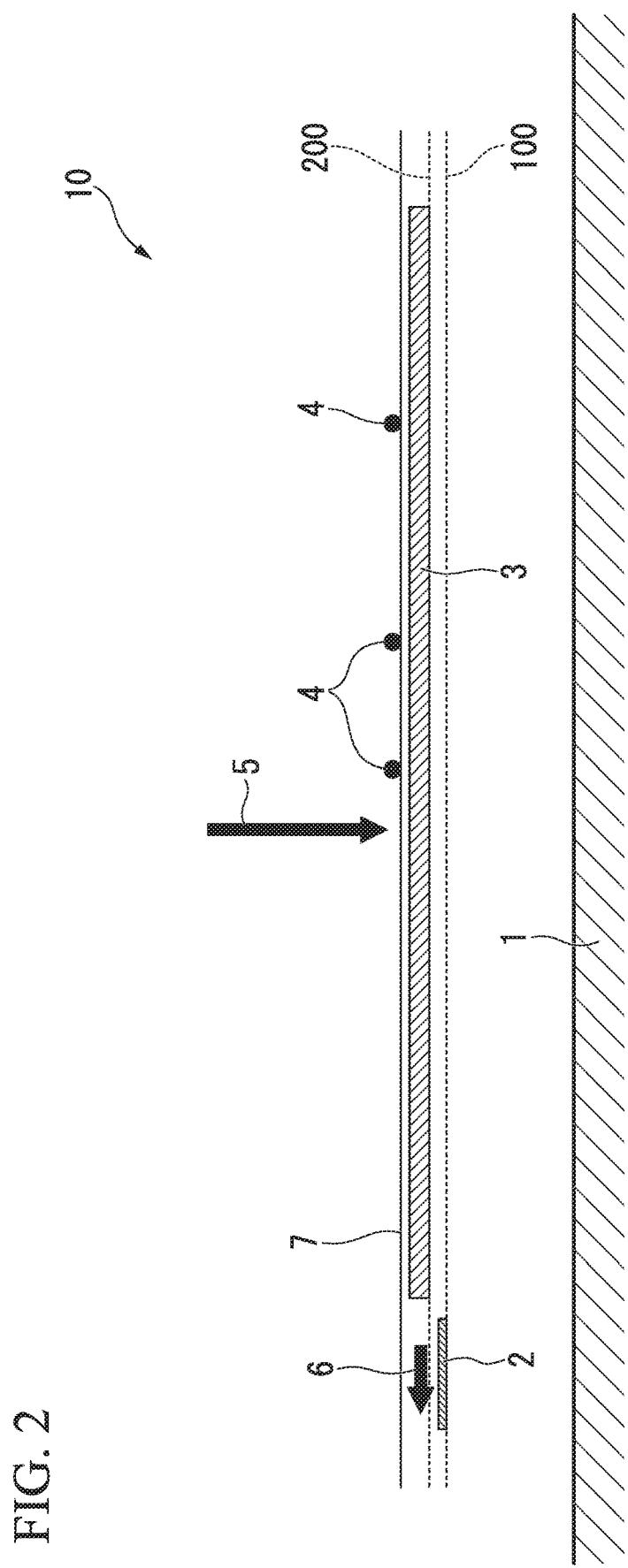
FIG. 2 is a cross-sectional view of the biosensor according to a first embodiment taken along line II-II of FIG. 1.

FIG. 1 is a perspective view of a main part of the biosensor of the first embodiment, and FIG. 2 is a cross-sectional view taken along line II-II of FIG. 1. The first plane, the second plane, the third plane, and the fourth plane described below are virtual planes, which are introduced for the sake of convenience in order to define the positional relationship of the members on the plane.

The biosensor 10 of the present embodiment detects biomolecules in a sample.

The biosensor 10 includes a substrate 1, a magnetoresistance element 2 whose resistance value measured changes depending on a direction of an input magnetic field, a soft magnetic thin film 3 disposed adjacent to the magnetoresistance element 2, and a protective film 7 for covering the surface of the soft magnetic thin film 3, in which the protective film 7 is provided on the outer surface thereof with a first affinity substance for recognizing the biomolecules.

Further, in the present embodiment, magnetic beads 4, each having a second affinity substance that recognizes a site different from the biomolecule recognition site of the first affinity substance, are accumulated on the protective film 7 through a first affinity substance-biomolecule-second affinity substance complex, and in the case where a magnetic field (applied magnetic field 5) is applied in a direction crossing the soft magnetic thin film 3, a detection magnetic field 6 (leakage magnetic field) is input to the magnetoresistance element 2.

As shown in FIG. 2, the magnetoresistance element 2 is disposed on a first plane 100 that is positioned away from the main surface of the substrate 1 and is substantially parallel to the main surface of the substrate 1. A soft magnetic thin film 3 is disposed on a second plane 200 that is positioned further away from the main surface of the substrate 1 than the first plane 100. That is, in the present embodiment, the main surface of the magnetoresistance element 2 opposite to the substrate 1 and the main surface of the soft magnetic thin film 3 opposite to the substrate 1 are disposed at different positions in the normal direction to the substrate 1.

The surface of the soft magnetic thin film 3 is covered with the protective film 7 and the outer surface of the protective film 7 is provided with a first affinity substance that captures biomolecules to be detected. Magnetic beads 4 are also provided with a second affinity substance that captures biomolecules. The first affinity substance and the second affinity substance recognize different sites in the biomolecules from each other. That is, it enables the formation of a first affinity substance-biomolecule-second affinity substance complex.

Further, an electrode terminal (not shown) is disposed on a third plane (not shown) which is positioned further away from the main surface of the substrate 1 than the first plane and the second plane. The electrode terminal is connected to the magnetoresistance element 2 through an internal wiring (not shown).

The substrate 1 may be, for example, a substrate constituted of a semiconductor or conductor such as silicon or AlTiC, or an insulator such as alumina or glass, and the form thereof is not particularly limited.

The thickness of the substrate 1 is not particularly limited, but may be, for example, 400 µm or more and 2,000 µm or less. In the case where the thickness of the substrate 1 is within such a range, it is possible to obtain a biosensor having an appropriate strength, a reduced thickness and a light weight.

As used herein, the term "thickness of the substrate" refers to a thickness of an entire substrate. For example, the thickness of the substrate composed of a plurality of layers refers to a total thickness of all layers constituting the substrate.

It is preferable that the magnetoresistance element 2 disposed in the first plane 100 is a spin valve type element including a magnetization fixed layer having a magnetization direction fixed in a certain direction in the laminated surface and a magnetization free layer whose magnetization direction changes depending on an external magnetic field, and it is preferable that the magnetization fixed direction of the magnetization fixed layer is substantially parallel or substantially antiparallel to the leakage magnetic field that is a magnetic field input from the end face of the soft magnetic thin film, and is in the film surface direction of the magnetoresistance element.

In the present embodiment, the phrase "substantially parallel or substantially antiparallel" may be approximately parallel or antiparallel and may be deviated within a range of 0.1° or more and 10° or less.

Further, the magnetoresistance element 2 more preferably has a laminate including a magnetization fixed layer, an intermediate layer constituted of a non-magnetic conductor or insulator, and a magnetization free layer, with the intermediate layer being sandwiched between the magnetization fixed layer and the magnetization free layer.

In the case where the intermediate layer is constituted of a conductor, the magnetoresistance element 2 is generally referred to as a giant magnetoresistance element (GMR), and in the case where the intermediate layer is constituted of an insulator, the magnetoresistance element 2 is referred to as a tunneling magnetoresistance element (TMR). The resistance of the magnetoresistance element 2 varies according to the angle between the magnetization direction of the magnetization fixed layer and the average magnetization direction of the magnetization free layer. In general, the magnetization direction of the magnetization fixed layer is defined as the magnetosensitive direction.

The magnetization free layer is constituted of, for example, a soft magnetic film of NiFe or the like. The intermediate layer is constituted of, for example, a conductive film of Cu or the like, or an insulating film of alumina, magnesium oxide, or the like.

The magnetization fixed layer is constituted of an antiferromagnetic film and a magnetization fixed film, and the magnetization fixed film is in contact with the intermediate layer. The antiferromagnetic film is formed of, for example, an antiferromagnetic Mn alloy such as IrMn or PtMn. The magnetization fixed film may be formed of, for example, a ferromagnetic material such as CoFe or NiFe, or may take a configuration in which a thin film layer of Ru is sandwiched between CoFe, or the like.

The soft magnetic thin film 3 has a function of changing the direction of a magnetic field (applied magnetic field 5) applied substantially in the normal direction of the laminated surface and generating a magnetic field component of the magnetosensitive direction of the magnetoresistance element 2 as a leakage magnetic field (detection magnetic field 6) at the end of the laminated surface of the soft magnetic thin film 3, and a function of transmitting a lamination in-plane direction component of a stray magnetic field of the magnetic beads 4 accumulated on the soft magnetic thin film 3 to the magnetoresistance element 2.

It is preferable that the soft magnetic thin film 3 is disposed on the same straight line along the magnetization fixed direction of the magnetoresistance element 2 as seen from the direction of application of the magnetic field applied to the soft magnetic thin film 3. Further, although FIG. 2 shows the case where the soft magnetic thin film 3 and the magnetoresistance element 2 do not overlap as seen in plan view from the direction of the applied magnetic field 5 (the direction indicated by reference numeral 5 in FIG. 2) (the soft magnetic thin film 3 and the magnetoresistance element 2 do not overlap each other in the case of being projected on a plane parallel to the substrate 1), as shown in Example 3 described later, the soft magnetic thin film 3 may be disposed so as to overlap with the magnetoresistance element 2 as seen in plan view from the direction of the applied magnetic field 5, or the soft magnetic thin film 3 may be disposed so as to be in contact with the magnetoresistance element 2 as seen from a plan view from the direction of the applied magnetic field 5. From the viewpoint of the sensitivity of the biosensor (the magnitude of the magnetic field received by the magnetoresistance element per magnetic bead), it is most preferable to dispose them so as to be in contact with each other, which is preferably followed by a case of disposing them so as to overlap each other and a case of disposing them so as not to overlap each other in this order (see FIG. 6 (A)). On the other hand, from the viewpoint of ease of manufacture, it is preferable that the soft magnetic thin film 3 is disposed so as to overlap with the magnetoresistance element 2 as seen from a plan view.

For example, permalloy or the like is preferable as the soft magnetic thin film 3.

The protective film 7 constituted of an insulating film is formed at least on the soft magnetic thin film 3. The material for the protective film 7 is preferably, for example, an inorganic material such as alumina, aluminum nitride, silicon oxide, or silicon nitride, or an organic material such as polyimide.

The size of the soft magnetic thin film 3 is appropriately selected depending on the number and size of the magnetic beads 4 to be captured, but it is preferably 0.1 µm square or more and 1,000 µm square or less, more preferably 0.5 µm square or more and 500 µm square or less, and particularly preferably 50 µm square or more and 200 µm square or less.

The thickness of the soft magnetic thin film 3 is preferably 0.01 µm or more and 100 µm or less, more preferably 0.1 µm or more and 50 µm or less, and particularly preferably 0.5 µm or more and 5 µm or less.

The magnetic beads 4 are not particularly limited as long as they are magnetic particles, and examples thereof include iron oxide particles. The diameter of the magnetic beads 4 depends on the balance with the area of the protective film 7, but it is, for example, preferably 0.01 µm or more and 100 µm or less, more preferably 0.05 µm or more and 50 µm or less, and particularly preferably 0.1 µm or more and 5 µm or less.

The magnetic beads 4 have a second affinity substance that specifically binds to biomolecules and captures the biomolecules through the second affinity substance. The magnetic beads 4 may be one to which a second affinity substance is added by a coating treatment or the like or may be constituted of a second affinity substance itself.

The surface of the magnetic beads 4 is preferably coated with a polymer or silica matrix, depending on the biomolecules to be captured. In the case where it is desired to capture a ligand as the biomolecule, the surface of the magnetic beads 4 is preferably hydrophilic. In the case where it is desired to capture an antibody as the biomolecule, the surface of the magnetic beads 4 is preferably hydrophobic.

The outer surface of the protective film 7 is a surface that comes into contact with biomolecules in a sample. The outer surface has a first affinity substance that specifically binds to biomolecules to be detected. In addition, the magnetic beads 4 also have a second affinity substance that specifically binds to the biomolecules.

By providing these affinity substances, biomolecules are fixed on the outer surface of the protective film 7 through the first affinity substance only in the case where the biomolecules to be detected are present in a sample (in an analyte), and subsequently, the magnetic beads 4 are bonded to the biomolecules through the second affinity substance, whereby the magnetic beads 4 are fixed on the surface of the protective film 7.

Examples of biomolecules to be detected include nucleic acids (which may be naturally occurring or may be chemically synthesized) such as DNA, mRNA, miRNA, siRNA, and artificial nucleic acids (for example, Locked Nucleic Acid (LNA) and Bridged Nucleic Acid (BNA)), peptides such as ligands, cytokines and hormones; proteins such as receptors, enzymes, antigens and antibodies; cells, viruses, bacteria, and fungi.

Examples of the sample containing biomolecules to be detected include blood, serum, plasma, urine, buffy coat, saliva, semen, pleural exudate, cerebrospinal fluid, tears, sputum, mucus, lymph fluid, ascites, pleural effusion, amniotic fluid, bladder lavage fluid, bronchoalveolar lavage fluid, cell extract, and cell culture supernatant.

Further, as the biomolecule to be detected, a biomolecule to be detected may be complexed with another biomolecule, or a biomolecule to be detected may be converted into another biomolecule. For example, a complex obtained by complexing biotin-terminated DNA with RNA by hybridization (hereinafter, sometimes referred to as "RNA-DNA-biotin complex"), or the like can be mentioned. By adding biotin to RNA by complexation, it becomes possible to specifically bind to streptavidin. Therefore, for example, by using RNA or DNA that can hybridize to the RNA contained in the RNA-DNA-biotin complex or the nucleic acid portion to which the DNA is not hybridized as the first affinity substance, the biomolecule to be detected can be captured on the biosensor of the present embodiment, and by further using streptavidin as the second affinity substance, the RNA-DNA-biotin complex can be specifically detected.

In the case where the biomolecule to be detected is a nucleic acid, examples of the first affinity substance and the second affinity substance that specifically bind to the biomolecule include nucleic acids complementary to such a nucleic acid. In the case where the biomolecule to be detected is an antigen, examples of the first affinity substance and the second affinity substance include antibodies having an affinity for such an antigen. In the case where the biomolecule to be detected is a primary antibody, examples of the first affinity substance and the second affinity substance include antigens and secondary antibodies having an affinity for such a primary antibody. In the case where the biomolecule to be detected is a cell, a virus, a bacterium, a fungus, or the like, examples of the first affinity substance and the second affinity substance include antibodies recognizing an antigen presented on the surface thereof.

In the case where the biomolecule to be detected is miRNA present in the blood, the first affinity substance may be, for example, a first nucleic acid complementary to 10 bases of the 5' end of such miRNA, and the second affinity substance may be, for example, a second nucleic acid complementary to 10 bases of the 3' end of such miRNA.

In the case where the biomolecule to be detected is an antigen protein present in the blood, the first affinity substance may be, for example, a first antibody that recognizes such an antigen protein, and the second affinity substance may be, for example, a second antibody that recognizes such an antigen protein and has a different epitope from the first antibody.

In the above description, an example has been made in which the magnetic beads 4 are bonded to the biomolecules fixed on the surface of the protective film 7. However, the disclosure is not limited thereto, and biomolecules to be detected may be bonded to the magnetic beads 4 in advance and the resulting structure as a sample may be brought into contact with the surface of the protective film 7.

Any conventional techniques or techniques to be developed in the future can be applied to the method of fixing the magnetic beads 4 on the surface of the protective film 7 covering the soft magnetic thin film 3. Any method may be used as long as it is configured so as to indirectly detect the presence of a biomolecule to be detected by measuring the magnetic beads 4. It is preferable that the surface of the protective film 7 above the magnetoresistance element 2 is not provided with the first affinity substance that specifically binds to the biomolecule to be detected.

An electrode terminal (not shown) is disposed on a third plane (not shown) and connected to the magnetoresistance element 2 through an internal wiring (not shown), and the resistance change of the magnetoresistance element 2 can be taken out as an output. As the material for the electrode terminal and the internal wiring, conductive metals such as Au, Al, Ag, and Cu, alloys thereof, and the like are preferable.

The magnetoresistance element 2, the soft magnetic thin film 3 and the electrode terminal are separated by an insulating layer (not shown), so that it is possible to prevent an electrical short circuit between the respective parts. In the case where the substrate 1 is of a conductive material, an insulating layer is formed on the main surface of the substrate 1, and therefore it is possible to prevent an electrical short circuit through the substrate 1. As the material for the insulating layer, an inorganic material such as alumina, aluminum nitride, silicon oxide, or silicon nitride, or an organic material such as polyimide is preferable.

In the case where the magnetic beads 4 are accumulated on the protective film 7 through the biomolecules and a magnetic field (applied magnetic field 5) is applied in a direction crossing the soft magnetic thin film 3, a detection magnetic field 6 (leakage magnetic field) is input to the magnetoresistance element 2. The direction of the applied magnetic field 5 is preferably perpendicular to the main surface of the magnetoresistance element 2. The applied magnetic field 5 is not particularly limited, but it is preferably 0.1 m tesla or more and 100 m tesla or less, and more preferably 1 m tesla or more and 10 m tesla or less. In the case where the applied magnetic field 5 is involved, the leakage magnetic field is preferably 1 n tesla or more and 10 m tesla or less, more preferably 10µ tesla or more and 5 m tesla or less, and particularly preferably 50µ tesla or more and 1 m tesla or less.

The detection magnetic field 6 (leakage magnetic field) is affected by the ratio of the magnetic beads 4 occupying the main surface of the magnetoresistance element 2 through the protective film 7. As the number of magnetic beads 4 accumulated on the protective film 7 increases, the detected resistance value increases. As will be described later in the Examples, the number of magnetic beads 4 accumulated on the protective film 7 and the resistance value measured through the leakage magnetic field are linearly correlated.

Then, according to the titer of the second affinity substance of the magnetic beads 4 (for example, the number of molecules of biomolecules captured by the second affinity substance), the number of molecules of the whole biomolecules accumulated on the protective film 7 can be calculated. That is, according to the present embodiment, the number of molecules of the biomolecules contained in a sample can be calculated. As described above, in the present embodiment, the quantitativeness of biomolecules in a sample can be secured with high accuracy.

In addition, the biosensor of the present embodiment exhibits high sensitivity and can detect up to several tens of nanotesla. Specifically, it is possible to detect an increase/decrease of 10 for 1,500 magnetic beads. That is, a change of about 0.5% can be detected.

Further, since the biosensor of the present embodiment uses magnetic beads, it has higher sensitivity and longer lifetime than fluorescence. Therefore, it is far superior to detection means such as ELISA.

<Second Embodiment>

Figure 3:
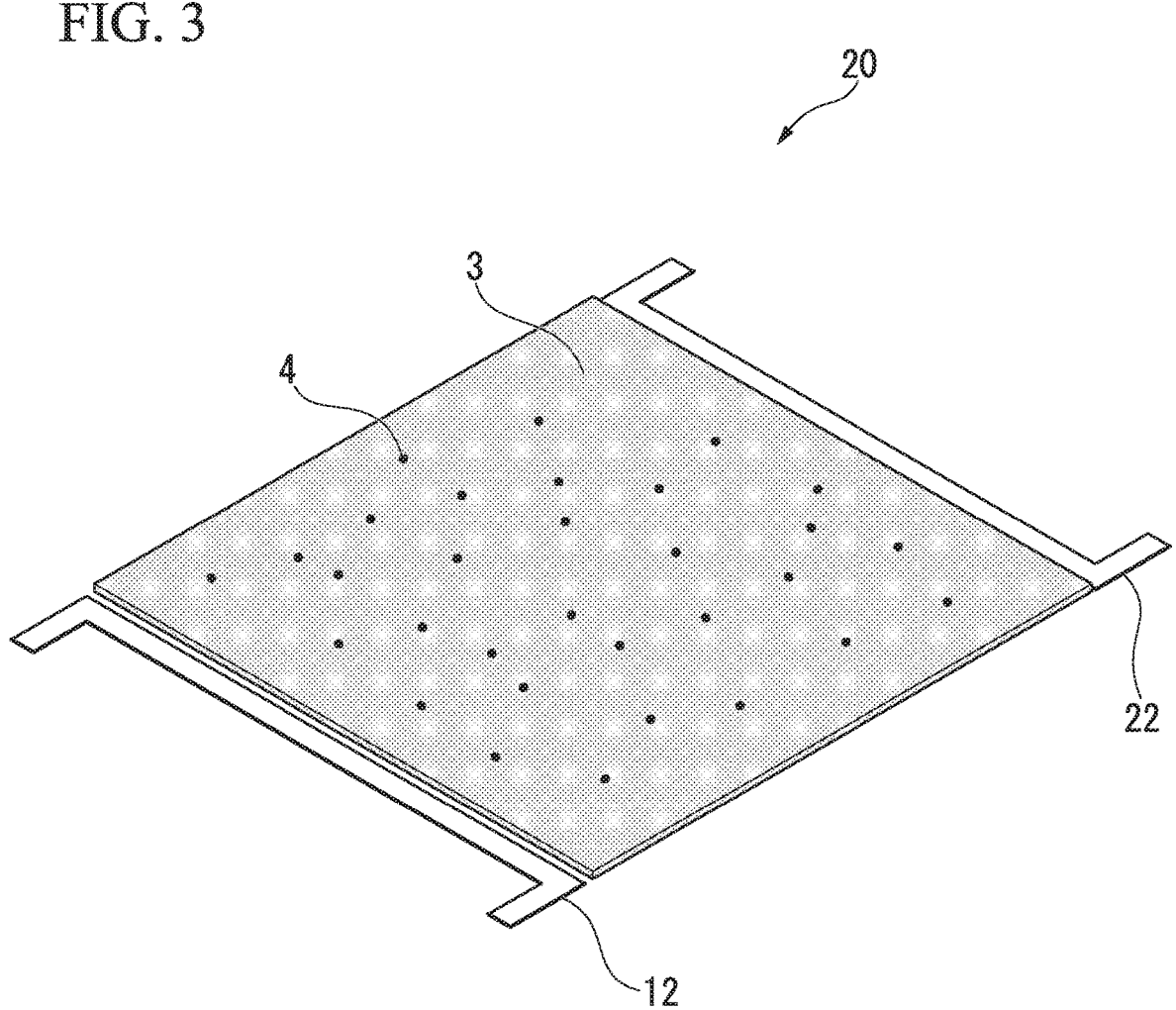
FIG. 3 is a perspective view of a biosensor according to a second embodiment.

FIG. 3 is a perspective view of a main part of the biosensor according to the second embodiment.

In a biosensor 20 of the present embodiment, the magnetoresistance element includes a first magnetoresistance element 12 and a second magnetoresistance element 22, one of the first and second magnetoresistance elements 12, 22 being positioned on one of end sides of the soft magnetic thin film 3 and other of the first and second magnetoresistance elements 12, 22 being positioned on other of the end sides of the soft magnetic thin film 3 to flank the soft magnetic thin film 3 between the first and second magnetoresistance elements 12, 22.

Further, the biosensor 20 of the present embodiment includes a half bridge circuit (not shown) configured to detect an operating voltage between connection points. In FIG. 3, the same components as those of the biosensor 10 shown in FIGS. 1 and 2 are denoted by the same reference numerals, and a description thereof will be omitted.

FIG. 3 is a perspective view of a main part of the biosensor according to the second embodiment. As shown in FIG. 3, in the present embodiment, the soft magnetic thin film 3 is disposed between the two magnetoresistance elements 12 and 22. The magnetization fixed directions of the respective magnetoresistance elements 12 and 22 are the same but the direction of the magnetosensitive direction component of the leakage magnetic field from the soft magnetic thin film 3 is in the opposite direction, and therefore the directions of resistance changes of the magnetoresistance elements 12 and 22 are in the opposite direction. Since a differential voltage is output at the midpoint connecting the two magnetoresistance elements 12 and 22 by connecting the two magnetoresistance elements 12 and 22 in series, it is possible to improve the magnetic field detection accuracy as compared to the biosensor of the first embodiment. Further, by combining two configurations of FIG. 3, a Wheatstone bridge circuit may be configured to further improve the detection accuracy.

As in the first embodiment, it is preferable that the first magnetoresistance element 12 and the second magnetoresistance element 22 are spin valve type elements having a magnetization fixed layer and a magnetization free layer, and it is preferable that the magnetization fixed direction of the magnetization fixed layer is substantially parallel or substantially antiparallel to the leakage magnetic field which is a magnetic field input from the end face of the soft magnetic thin film 3 and is in the film surface direction of the magnetoresistance element, and the magnetization fixed direction of the first magnetoresistance element 12 and the magnetization fixed direction of the second magnetoresistance element 22 are substantially parallel to each other. By using such a spin valve type element, biomolecules in a sample can be detected with higher sensitivity.

<Third Embodiment>

Figure 4:
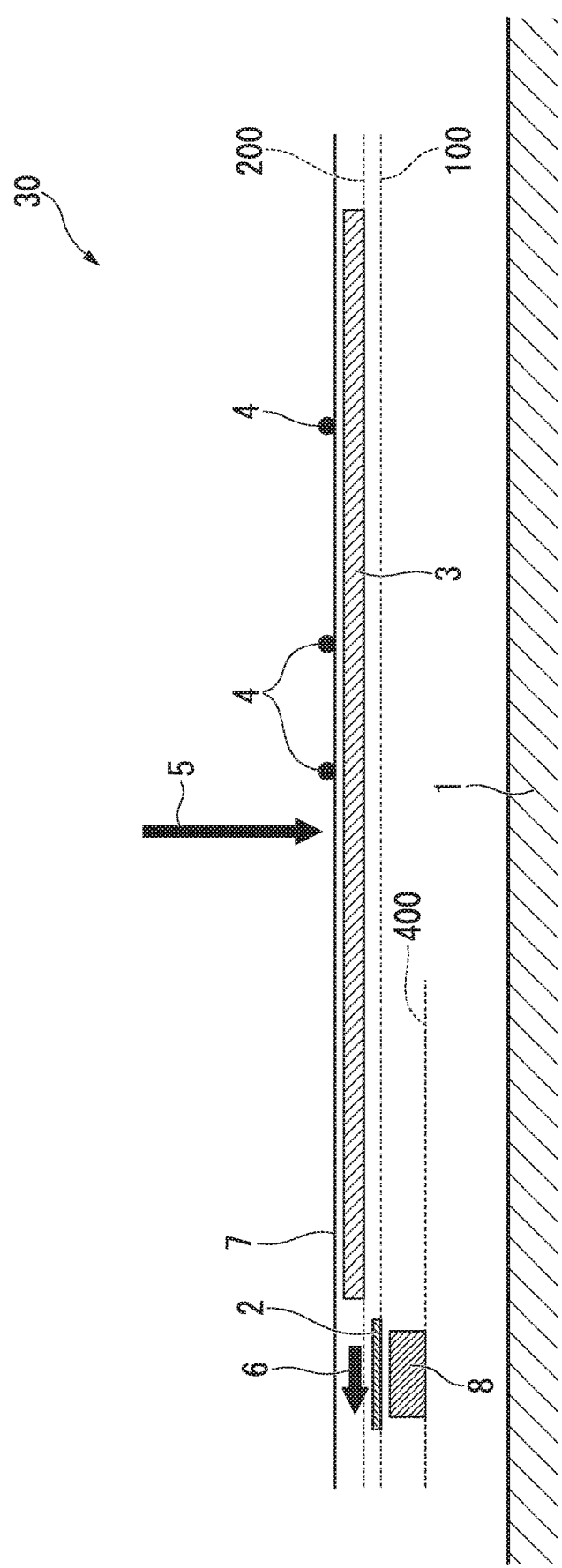
FIG. 4 is a cross-sectional view of a biosensor according to a third embodiment.

FIG. 4 is a cross-sectional view of the biosensor according to the third embodiment.

A biosensor 30 according to the present embodiment is configured such that a compensation current line 8 for applying a compensating magnetic field in a direction opposite to the magnetic field applied to the magnetoresistance element 2 based on the current to be detected, to the magnetoresistance element is provided between the magnetoresistance element 2 and the substrate 1.

As shown in FIG. 4, in the present embodiment, a compensation current line 8 is disposed, in addition to the first embodiment. The compensation current line 8 is disposed in a fourth plane 400 existing between the main surface of the substrate 1 and the first plane 100. A compensation current for applying a compensating magnetic field in a direction canceling the external magnetic field detected by the magnetoresistance element 2 to the magnetoresistance element 2 flows in the compensation current line 8. In the case where a compensation current is allowed to flow, a combined magnetic field of the external magnetic field to be detected and the compensating magnetic field is applied to the magnetoresistance element 2. The combined magnetic field includes a magnetosensitive direction component of the magnetoresistance element 2. The equilibrium point at which the magnetosensitive direction component of the combined magnetic field becomes zero is a point at which the magnetic field detection output of the magnetoresistance element 2 in the sensor of the present embodiment becomes zero. Since the magnitude of the compensation current at the time of reaching this equilibrium point is proportional to the external magnetic field to be detected, in the case where the value of the compensation current is known, the external magnetic field to be detected can be detected.

One end of the compensation current line 8 is connected to an electrode terminal (not shown) by an internal wiring (not shown) rising in the normal direction of the main surface of the substrate 1. By adopting such a configuration, adverse effects of unexpected changes in the resistance of the magnetoresistance element 2 due to ambient temperature or external noise can be reduced, so that the magnetic field detection accuracy is improved. The compensation current line 8 is formed of a conductor such as Cu and is separated from the magnetoresistance element 2 by an insulating layer (not shown). As the material for the insulating layer, an inorganic material such as alumina, aluminum nitride, silicon oxide, or silicon nitride or an organic material such as polyimide is preferable.

Further, as in the second embodiment, it is preferable in the present embodiment that the magnetoresistance element includes a first magnetoresistance element and a second magnetoresistance element. That is, the biosensor of the present embodiment is preferably configured such that a compensation current line configured to apply a compensating magnetic field in a direction opposite to each of the magnetic fields applied to the first magnetoresistance element and the second magnetoresistance element based on the current to be detected, to each of the first magnetoresistance element and the second magnetoresistance element is provided between the magnetoresistance element and the substrate. By such a configuration, the magnetic field detection accuracy is further improved.

[Method for Detecting Biomolecules]

<First Embodiment>

The method for detecting biomolecules of the present embodiment is a method for detecting biomolecules using the biosensor described above. The method for detecting biomolecules of the present embodiment includes a step 1 of bringing a sample containing the biomolecules into contact with the protective film to accumulate the biomolecules on the protective film through the first affinity substance; a step 2 of bringing the magnetic beads into contact with the protective film to accumulate the magnetic beads on the protective film through the biomolecules; and a step 3 of applying a magnetic field in a direction crossing the soft magnetic thin film to input a detection magnetic field to the magnetoresistance element and measuring a resistance value.

Individual steps will be described in detail.

<Step 1>

The step 1 is a step in which a sample containing biomolecules is brought into contact with a protective film to accumulate the biomolecules on the protective film through a first affinity substance. From the viewpoints such as convenience, the biosensor is preferably used in a microfluidic device. In the step 1, first, a sample containing biomolecules is allowed to flow into the microchannel. The sample is not particularly limited as long as it contains biomolecules to be detected. For example, in the case where the method for detecting biomolecules of the present embodiment is used for the diagnosis of a disease, examples of the sample include blood, lymph fluid, bone marrow aspirate, semen, saliva, and urine of a subject, such as a person from whom the onset of a disease is confirmed, a person suspected of having the onset of a disease, or a patient undergoing treatment for a disease.

For example, in the case where a peptide/protein such as an antigen or a receptor present on the surface of circulating tumor cells in the blood is to be detected, the sample may be allowed to flow in the microchannel as it is. For example, miRNA has been reported to be involved in the onset and progression of cancer, cardiovascular diseases, neurodegenerative diseases, psychiatric diseases, chronic inflammatory diseases, and the like. In the case where miRNA and other nucleic acids such as genomic DNA, cDNA, total RNA, mRNA, and rRNA are to be detected, it is preferable to extract a nucleic acid from blood, lymph fluid, bone marrow aspirate, semen, saliva, urine, or the like. The extraction method is appropriately selected from the conventional methods according to the type of nucleic acid.

Biomolecules in the sample flowing in the microchannel are captured by the first affinity substance on the protective film and accumulate on the protective film. As the first affinity substance, as described above, a nucleic acid, an antibody, or the like can be mentioned. The biomolecule forms a complex with the first affinity substance on the protective film by hybridization, antigen-antibody reaction, or the like.

After the first affinity substance-biomolecule complex is formed on the protective film, it is preferable to wash the protective film with a buffer or the like. Impurities non-specifically bound onto the protective film can be removed by washing, so that the detection accuracy of biomolecules can be improved.

<Step 2>

The step 2 is a step in which the magnetic beads are brought into contact with the protective film and accumulated on the protective film through biomolecules. As described above, the magnetic beads include a second affinity substance that captures biomolecules. For example, in the case where magnetic beads flow through the microchannel and come into contact with the protective film, the magnetic beads bind to the biomolecules in the first affinity substance-biomolecule complex formed on the protective film through the second affinity substance. By the step 2, a first affinity substance-biomolecule-second affinity substance complex is formed on the protective film. That is, magnetic beads having a second affinity substance accumulate on the protective film.

After forming the first affinity substance-biomolecule-second affinity substance complex on the protective film, it is preferable to wash the protective film with a buffer or the like as in the step 1. The magnetic beads non-specifically bound onto the protective film can be removed by washing, so that the detection accuracy of the biomolecules can be improved.

<Step 3>

The step 3 is a step of applying a magnetic field in a direction crossing the soft magnetic thin film to input a detection magnetic field to the magnetoresistance element and measuring a resistance value.

The detection magnetic field (leakage magnetic field) is affected by the ratio of the magnetic beads occupying the main surface of the magnetoresistance element through the protective film. As the number of magnetic beads accumulated on the protective film increases, the detected resistance value increases.

By the step 3, the number of magnetic beads accumulated on the protective film can be accurately quantified. Then, according to the titer of the second affinity substance of the magnetic beads (for example, the number of molecules of biomolecules captured by the second affinity substance), the number of molecules of the whole biomolecules accumulated on the protective film can be calculated. That is, according to the present embodiment, the number of molecules of the biomolecules contained in a sample can be calculated. Therefore, in the case where there is a positive correlation between the number of molecules of the biomolecules in the sample and the disease state, it is possible to observe the progress of the disease state by successively calculating the number of molecules of the biomolecules in the sample.

As described above, in the present embodiment, the quantitativeness of biomolecules in a sample can be secured.

<Second Embodiment>

The method for detecting biomolecules of the present embodiment includes a step 4 of mixing a sample containing biomolecules with magnetic beads and capturing the biomolecules on the magnetic beads through a second affinity substance; a step 5 of bringing the biomolecule-captured magnetic beads into contact with a protective film to accumulate the magnetic beads on the protective film through the biomolecules; and a step 3 of applying a magnetic field in a direction crossing the soft magnetic thin film to input a detection magnetic field to the magnetoresistance element and measuring a resistance value.

The second embodiment is the same as in the first embodiment, except that a biomolecule-second affinity substance complex is formed first at the time of forming the first affinity substance-biomolecule-second affinity substance complex, so that the description of individual steps will be omitted.

[Biochip]

The biochip of the present embodiment is provided with the above-described biosensor.

By providing a plurality of biosensors having different first affinity substances to be provided on the protective film, it is possible to comprehensively analyze the properties of the sample.

Examples of the biochip of the present embodiment include a biochip for cancer diagnosis, a biochip for diagnosis by carcinoma, and a biochip for detecting an influenza virus.

<Biochip for Cancer Diagnosis>

The first affinity substance provided on the protective film may be, for example, a nucleic acid complementary to a nucleic acid derived from a cancer gene or a cancer suppressor gene. In the case where a mutation unique to a cancer patient is present in the cancer gene or cancer suppressor gene, preferable is a nucleic acid complementary to a nucleic acid containing such a mutation.

Examples of the cancer gene include genes encoding a growth factor such as sis; genes encoding a receptor-type tyrosine kinase such as erbB, fms, and ret; genes encoding a non-receptor type tyrosine kinase such as fes; genes encoding a GTP/GDP binding protein such as ras; genes encoding serine/threonine kinase such as src, mos, and raf; genes encoding an intranuclear protein such as myc, myb, fos, jun, and erbA; genes encoding a signal transduction adapter molecule such as crk; and fusion genes such as Bcr-Abl.

Further examples of the cancer gene include Ras-MAP kinase pathway-related genes such as Shc, Grb2, Sos, MEK, Rho, and Rac genes; phospholipase C gamma-protein kinase C pathway-related genes such as PLCγ and PKC; PI3K-Akt pathway-related genes such as PI3K, Akt, and Bad; JAK-STAT pathway-related genes such as JAK and STAT; and GAP pathway-related genes such as GAP, p180, and p62.

Examples of the cancer suppressor gene include RB, p53, WT1, NF1, APC, VHL, NF2, p16, p19, BRCA1, BRCA2, PTEN, and E cadherin genes.

In addition, the first affinity substance may be a substance that captures a protein which is a gene product of the above-mentioned gene, for example, an antibody, a ligand, or a receptor.

<Biochip for Diagnosis by Carcinoma>

In the biochip of the present embodiment, the first affinity substance provided on the protective film may be a nucleic acid complementary to a plurality of nucleic acids extracted from one type of carcinoma. That is, the biochip of the present embodiment may be a biochip for diagnosis by carcinoma.

Examples of the carcinoma include skin cancer, lung cancer, colon cancer, stomach cancer, breast cancer, prostate cancer, and thyroid cancer. It has been reported that expression/mutation patterns of carcinoma-specific genes, including the above-mentioned cancer genes and cancer suppressor genes, are present. Therefore, the accuracy of diagnosis can be enhanced by preparing the biochip of the present embodiment according to the gene expression profile or the like of each carcinoma.

Further, by using the biochip of the present embodiment, it is possible to predict the sensitivity/resistance to an anticancer agent. For example, in the case of gefitinib which is an EGFR inhibitor, it has been reported that in the case where EGFR in a test sample has an L858R mutation or a G719X mutation, it exhibits sensitivity to gefitinib.

On the other hand, in the case where EGFR in a sample to be tested has a T790M mutation and/or a D761Y mutation, it has been reported to exhibit resistance to gefitinib. In addition, it has been reported that these mutations exhibiting gefitinib resistance are detected more frequently as the stage progresses. According to the present embodiment, it is also possible to investigate the degree of cancer progression, from the viewpoint that the biochip of the present embodiment can easily quantify the EGRF gene exhibiting a resistance mutation.

<Biochip for Detecting Influenza Virus>

In the biochip of the present embodiment, the first affinity substance provided on the protective film may be a nucleic acid complementary to a nucleic acid derived from an influenza virus. That is, the biochip of the present embodiment may be a biochip for detecting an influenza virus.

Examples of the biochip of the present embodiment include those in which a nucleic acid recognizing a mutated site such as a reported mutation, in the genome of each of type A, type B, and type C viruses, is fixed on a protective film. The first affinity substance may be an antibody capable of specifically recognizing each of the type A, type B, and type C viruses.

According to the present embodiment, infection of influenza viruses can be detected at an early stage.

Further, by using the biochip of the present embodiment over time, it is possible to observe the progress of the disease state after the viral infection.

EXAMPLES

Hereinafter, the disclosure will be described in more detail with reference to Examples and Comparative Examples, but the disclosure is not limited to these Examples and the like.

Example 1

Using the biosensor of the third embodiment shown in FIG. 4, the correlation between the number of magnetic beads placed on the protective film and the detected voltage was confirmed. Dynabeads M-270 having a diameter of 2.8 μm was used as the magnetic bead. As for the magnetoresistance element, two GMR thin lines (100 μm in line length and 2 μm in line width) were connected to a half bridge circuit. The voltage of the GMR half bridge was set to 0.63 V.

The film structure of GMR is as shown in Table 1.

TABLE 1

|  |  | Material | t (Å) |
|---|---|---|---|
|  | Cap layer | Ta | 20 |
|  |  | Ru | 5 |
|  | Magnetization free layer | NiFe | 70 |
|  |  | $Co_{90}Fe_{10}$ | 10 |
|  | Intermediate layer | Cu | 21 |
| Pin layer | In-Pin | $Co_{90}Fe_{10}$ | 16 |
|  | Intermediate layer | Ru | 8 |
|  | Out-Pin | $Co_{90}Fe_{10}$ | 5 |
|  |  | $Co_{30}Fe_{70}$ | 5 |
|  |  | $Co_{90}Fe_{10}$ | 5 |
|  | Antiferromagnetic layer | IrMn | 70 |
|  | Buffer layer | NiCr | 50 |
|  | Substrate |  |  |

Figure 5:
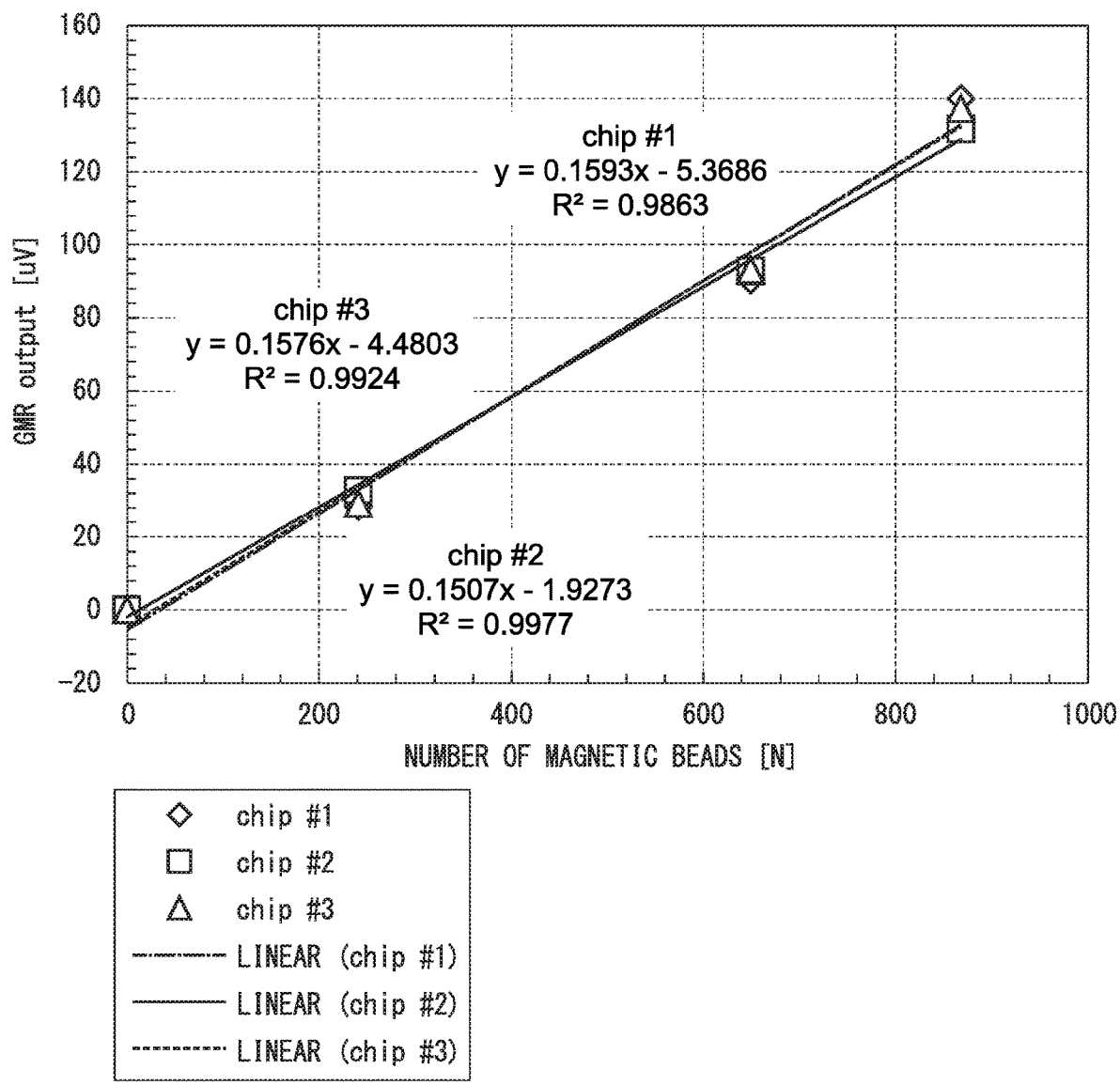
FIG. 5 shows the results of Example 1.
Figure 7:
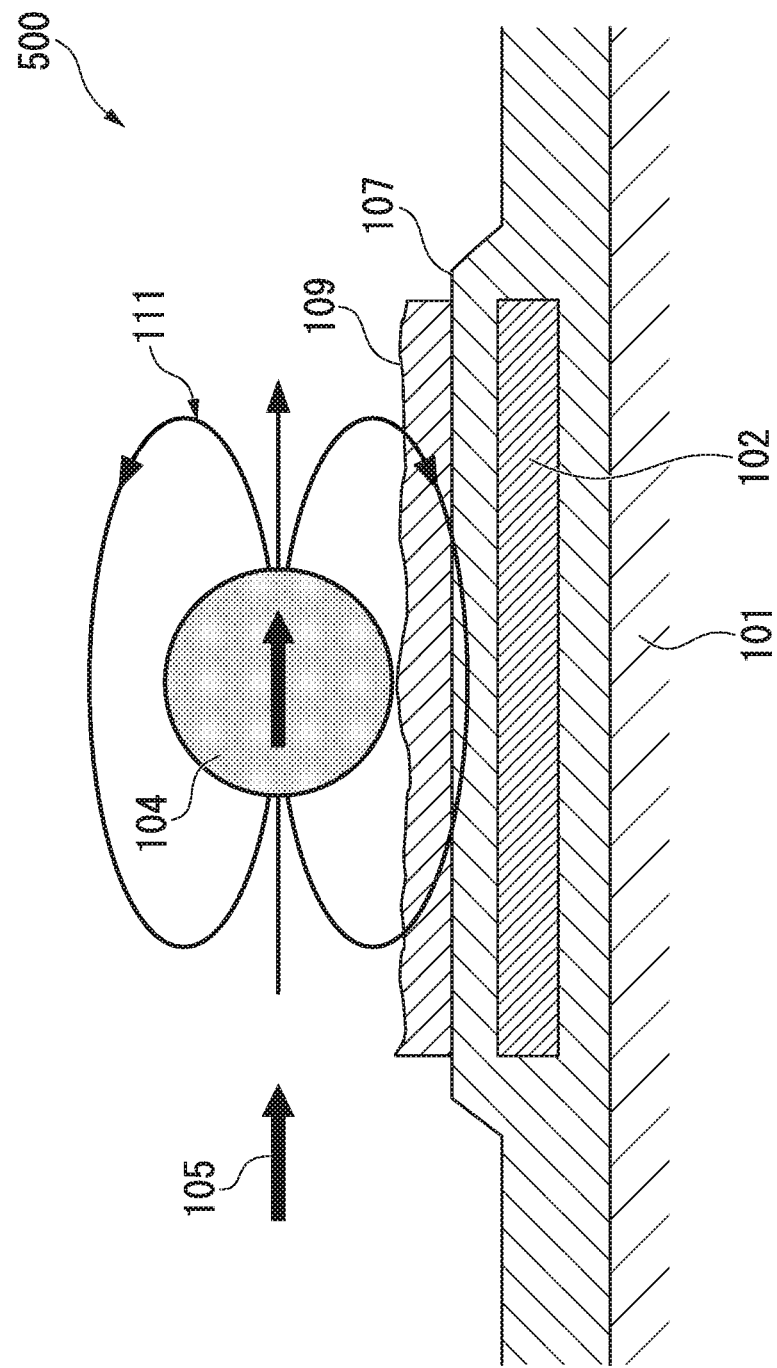
FIG. 7 is a cross-sectional view of a conventional magnetic detection type biosensor.
Figure 8:
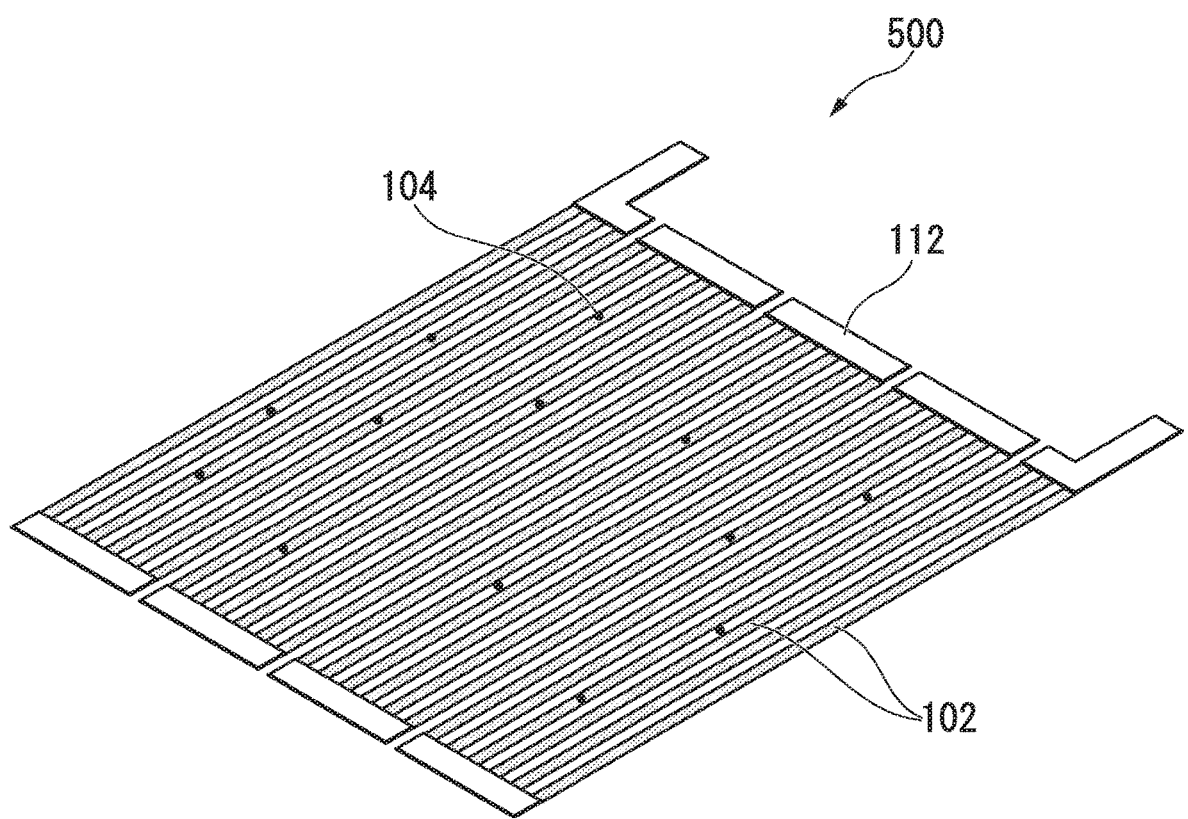
FIG. 8 is a perspective view of a conventional magnetic detection type biosensor.

The number of magnetic beads placed on the protective film was plotted on the horizontal axis, and taking the voltage at which the number of magnetic beads placed on the protective film is zero as a reference voltage, the value of measured voltage-reference voltage was plotted on the vertical axis. The results are shown in FIG. 5, and specific numerical values are shown in Table 2. Three biosensors were fabricated and tested independently (chip #1, chip #2, and chip #3).

TABLE 2

| beads [N] | chip #1 [μV] | chip #2 [μV] | chip #3 [μV] |
|---|---|---|---|
| 868 | 140 | 131.6 | 137.2 |
| 649 | 90.2 | 92.7 | 93 |
| 241 | 28.3 | 32.8 | 29 |
| 0 | 0 | 0 | 0 |
| Sensitivity [μV/particle] | 0.1593 | 0.1507 | 0.1576 |
| Correlation coefficient | 0.9863 | 0.9977 | 0.9924 |

As shown in FIG. 5 and Table 2, a linear correlation was confirmed between the number of magnetic beads placed on the protective film and the detected voltage. The correlation coefficient was 0.98 or more, and the sensitivity (voltage increasing per particle) was about 0.15 μV.

Example 2

Using the biosensor (chip #2) fabricated in Example 1, the voltage at which the number of magnetic beads placed on the protective film is zero was measured three times and 3σ was calculated. The sensitivity obtained in Example 1 was used to calculate 3σ/sensitivity. Detailed numerical values are shown in Table 3. The total number of magnetic beads with a diameter of 2.8 μm placed on the protective film of 100 μm square was calculated as 1275. The 3σ/sensitivity was divided by the total number, and the ratio of the counting error to the total number was calculated as 0.578%.

TABLE 3

|  | chip #2 [μV] |
|---|---|
| repeat #1 | 184.6499 |
| repeat #2 | 184.5878 |
| repeat #3 | 183.98 |
| Average | 184.4059 |
| 3σ | 1.110435 |
| 3σ/sensitivity | 7.369119 |

Example 3

As shown in FIGS. 6 (A) and 6 (B), by using a biosensor in which the overlap (−0.5 μm or 1 μm) between the magnetoresistance element and the soft magnetic thin film is different, the correlation between the distance between the magnetoresistance element and the soft magnetic thin film and the magnetic field received by the magnetoresistance element (per magnetic bead) was confirmed. Dynabeads M-270 having a diameter of 2.8 μm was used as the magnetic bead. As for the magnetoresistance element, one GMR thin line (100 μm in line length and 2 μm or 5 μm in line width) was connected to a half bridge circuit. The voltage of the GMR half bridge was set to 0.63 V.

The film structure of GMR is the same as in Table 1 above.

The distance between the magnetoresistance element and the soft magnetic thin film was plotted on the horizontal axis and the magnetic field received by the magnetoresistance element (per magnetic bead) was plotted on the vertical axis. The results are shown in FIG. 6 (A). In FIG. 6 (A), the "GMR width=2 μm (sim.)" is a plot of the predicted values in the simulation in the case where the line width of the GMR thin line is 2 μm and the "GMR width=2 μm (exp.)" is a plot of actual measured values in the case where the line width of the GMR thin line is 2 μm. Similarly, the "GMR width=5 μm (sim.)" is a plot of the predicted values in the simulation in the case where the line width of the GMR thin line is 5 μm, and the "GMR width=5 μm (exp.)" is a plot of actual measured values in the case where the line width of the GMR thin line is 5 μm.

From FIG. 6 (A), in the case where the overlap between the magnetoresistance element and the soft magnetic thin film was −0.5 μm in the actual measured value in the case where the line width of the GMR thin line was 2 μm, the magnetic field received by the magnetoresistance element (per magnetic bead) was about 48 nT, whereas in the case where the overlap between the magnetoresistance element and the soft magnetic thin film was 1 μm, the magnetic field received by the magnetoresistance element (per magnetic bead) was about 40 nT.

Further, in the case where the overlap between the magnetoresistance element and the soft magnetic thin film was −0.5 μm in the actual measured value in the case where the line width of the GMR thin line was 5 μm, the magnetic field received by the magnetoresistance element (per magnetic bead) was about 36 nT, whereas in the case where the overlap between the magnetoresistance element and the soft magnetic thin film was 1 μm, the magnetic field received by the magnetoresistance element (per magnetic bead) was about 28 nT.

Also, even in the case where the line width of the GMR thin line was 2 μm or 5 μm, there was no significant difference between the measured value and the predicted value in the simulation.

Therefore, it was confirmed in the biosensor of the disclosure that the magnetic field received by the magnetoresistance element (per magnetic bead) was increased by about 20% to 30% as a part of the magnetoresistance element and the soft magnetic thin film overlap.

INDUSTRIAL APPLICABILITY

According to the disclosure, it is possible to provide a sensor with high accuracy and high sensitivity, a method for detecting biomolecules using the sensor, and a biochip using the sensor. In addition, by providing a plurality of sensors having different first affinity substances to be provided on the protective film, it is possible to provide a biochip capable of comprehensively analyzing the properties of the sample. Specifically, as the biochip of the disclosure, it is possible to provide a biochip for cancer diagnosis, a biochip for diagnosis by carcinoma, a biochip for detecting an influenza virus, and the like.

What is claimed is:

1. A sensor, comprising:
   a substrate;
   a first magnetoresistance element and a second magnetoresistance element, each of which is a magnetoresistance element whose resistance value measured changes depending on a direction of an input magnetic field; and
   a soft magnetic thin film disposed adjacent to the first and second magnetoresistance elements;
   wherein one of the first and second magnetoresistance elements is positioned on one of end sides of the soft magnetic thin film and other of the first and second magnetoresistance elements is positioned on other of the end sides of the soft magnetic thin film in a plan view in a direction perpendicular to a film surface of the soft magnetic thin film.

2. The sensor according to claim 1, wherein the sensor further includes a half bridge circuit configured to detect an operating voltage between connection points.

3. The sensor according to claim 1, wherein each of the first magnetoresistance element and the second magnetoresistance element is a spin valve type elements having a magnetization fixed layer and a magnetization free layer,
   a magnetization fixed direction of the magnetization fixed layer of each of the first and second magnetoresistance elements is: substantially parallel or substantially anti-parallel to the leakage magnetic field which is a magnetic field input from an end face of the soft magnetic thin film; and is in a film surface direction of each of the first and second magnetoresistance elements, and
   the magnetization fixed direction of the first magnetoresistance element and the magnetization fixed direction of the second magnetoresistance element are substantially parallel to each other.

4. The sensor according to claim 1, further comprising:
   a compensation current line disposed between one of the first and second magnetoresistance elements and the substrate, the compensation current line being configured to apply a compensating magnetic field to the one of the first and second magnetoresistance elements in a direction opposite to a magnetic field applied to the one of the first and second magnetoresistance elements.

5. The sensor according to claim 1, wherein a main surface of each of the first and second magnetoresistance elements opposite to the substrate and a main surface of the soft magnetic thin film opposite to the substrate are disposed at different positions in the normal direction to the substrate.

6. A biochip comprising the sensor according to claim 1.

* * * * *